United States Patent [19]

Naumann et al.

[11] Patent Number: 5,733,897
[45] Date of Patent: Mar. 31, 1998

[54] IMIDOBISPHOSPHORIC ACIDS, AND USE THEREFOR

[75] Inventors: Christoph Naumann, Niedernhausen, Germany; Katsuhiro Yoshikawa, Kawagoe, Japan; Kazuyuki Kitamura, Sakado, Japan; Mizuho Inazu, Iruma, Japan

[73] Assignee: Hoechst Aktiengesellschaft, Frankfurt am Main, Germany

[21] Appl. No.: 525,104

[22] Filed: Sep. 8, 1995

[30] Foreign Application Priority Data

Oct. 4, 1994 [DE] Germany ............. 44 35 496.7

[51] Int. Cl.$^6$ .................. A61K 31/66; C07F 9/22
[52] U.S. Cl. ................... 514/102; 562/10
[58] Field of Search ................ 562/10; 514/102

[56] References Cited

U.S. PATENT DOCUMENTS 2,798,086  7/1957  Coover et al. .

FOREIGN PATENT DOCUMENTS 0620227  10/1994  European Pat. Off. .
1041044  10/1958  Germany .
9211269   7/1992  WIPO .

OTHER PUBLICATIONS

Ding et al., Chemical Abstract, 108(19):663, Abstract No. 167599, 'Organophosphorus compounds. XXI. Regioselective phosphorylation of ambident anions'.

Pinchuk et al., Reaction of N,N–Dichloro Amines with Phosphites and Phosphorochloridites. Translated from Zhurnal Obschei Khimii, vol.45, No. 11, pp. 2394–2396, Nov., 1975. Orginal article submitted Apr. 26, 1974.

Naumann et al., Phosphorus, Sulfur and Silicon, 91:169–177, 'Synthese Von Neuen Imidobisphosphorsäuren', (1994). (In German).

*Primary Examiner*—Robert W. Ramsuer
*Attorney, Agent, or Firm*—Finnegan, Henderson, Farabow, Garrett & Dunner, L.L.P.

[57] ABSTRACT

Imidobisphosphoric acids, process for their preparation, and use thereof.

There are described compounds of the formula I $$\begin{array}{c} R^1-N \begin{array}{c} P(=O)(O-R^2)(O-R^3) \\ P(=O)(O-R^4)(O-R^5) \end{array} \end{array} \quad (I)$$

in which $R^1$ is $(C_1-C_{10})$-alkyl, $(C_1-C_8)$-alkanoyl, $(C_6-C_{10})$-aryl or Het, each of which can be substituted by halogen, —OH, —NH$_2$, —NH—CO—R$^7$, —O—CO—R$^7$ and —N—(R$^8$)$_2$ where $R^7$=$(C_1-C_6)$-alkyl and $R^8$, independently of one another, is hydrogen or $(C_1-C_4)$-alkyl or in which $R^1$ is the radical of the formula II $$\text{(II)}$$

in which n is an integer from 3 to 10, m is zero to 3, $R^6$, independently of one another, is $(C_1-C_6)$-alkyl which is optionally substituted by halogen or —NH—CO—R$^7$, where $R^7$=$(C_1-C_6)$-alkyl, and X is absent or is $(C_1-C_{10})$-alkyl, and $R^2$, $R^3$, $R^4$ or $R^5$, independently of one another, are hydrogen, $(C_1-C_5)$-alkyl, lithium, sodium, potassium or Si(R), where R=$(C_1-C_5)$-alkyl, and their physiologically tolerable salts, a process for preparation of these compounds of the formula I and their use as pharmaceuticals in the prophylaxis and treatment of osteoporosis and hypercalcemia.

9 Claims, No Drawings

IMIDOBISPHOSPHORIC ACIDS, AND USE THEREFOR

Osteoporosis is a frequently occurring bone disorder. In the various forms of osteoporosis a severe loss of bone tissue occurs, so that finally the mechanical stability of the bone is lost. In healthy people, the rate at which osteoclasts and osteoplasts are formed is such that bone formation and bone resorption are in equilibrium. In osteoporosis the equilibrium is disturbed, so that breakdown of bone occurs.

EP-A 0 354 806, EP-A 0 546 548 and EP-A 0 522 576 describe the use of bisphosphonic acids for the treatment of bone disorders such as, for example, osteoporosis.

Riesel et al., Z. Anorg. Allg. Chem. 430, 227–233 (1977); Pinchuk et al., J. Gen. Chem. USSR, 45, 1975, 2352–2354; Arbuzov et al., IZU Akad. Nauk. SSSR Ser. Khim., 1956, 953–957 and Ger. Fed. Pat. 10 41 044 describe syntheses for the preparation of alkyl imidobisphosphates and U.S. Pat. No. 2,798,086 and Arbuzov et al., IZU Akad, Nauk. SSSR Ser. Khim., 1954, 913–916 disclose the use of individual alkyl imidobisphosphates as insecticides.

In the attempt to obtain active compounds for the simultaneous treatment and prophylaxis of degenerative joint disorders and osteoporosis with low side effects, it has now surprisingly been found that the imidobisphosphoric acids according to the invention in vitro inhibit calcium release from hydroxyapatite.

The invention therefore relates to compounds of the formula I

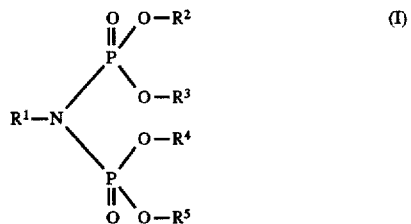

and their physiologically tolerable salts, where
$R^1$ is $(C_1-C_{10})$-alkyl, $(C_1-C_8)$-alkanoyl, $(C_6-C_{10})$-aryl or Het, each of which can be substituted one to six times by halogen, —OH, —NH$_2$, —NH—CO—R$^7$, —O—CO—R$^7$ and —N—(R$^8$)$_2$, where R$^7$ is $(C_1-C_6)$-alkyl and R$^8$, independently of one another, is hydrogen or $(C_1-C_4)$-alkyl, or the radical of the formula II

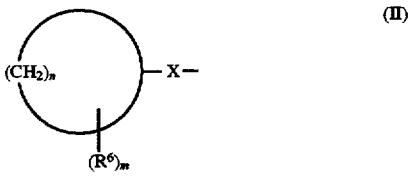

in which
n is an integer from 3 to 10,
m is zero to 3,
$R^6$, independently of one another, is $(C_1-C_6)$-alkyl, which is optionally substituted one to six times by halogen or —NH—CO—R$^7$ where R$^7$=$(C_1-C_6)$-alkyl and
X is absent or is $(C_1-C_{10})$-alkyl, and
$R^2$, $R^3$, $R^4$ or $R^5$, independently of one another, are hydrogen, $(C_1-C_6)$-alkyl, lithium, sodium, potassium or Si(R), where R=$(C_1-C_5)$-alkyl,
compounds of the formula I being excluded where
$R^1$=methyl and $R^2$–$R^5$ simultaneously=methyl, ethyl, propyl, isopropyl, butyl or isobutyl or $R^2$ and $R^3$=ethyl or isopropyl and $R^4$ and $R^5$=methyl, $R^1$=ethyl and $R^2$–$R^5$ simultaneously=ethyl, propyl, isopropyl, butyl or isobutyl or $R^2$ and $R^3$=ethyl and $R^4$ and $R^5$=methyl, $R^1$=isopropyl and $R^2$ and $R^3$=isopropyl and $R^4$ and $R^5$=methyl, $R^1$=butyl and $R^2$–$R^5$ simultaneously=ethyl, isopropyl or butyl, $R^1$=isobutyl and $R^2$–$R^5$ simultaneously=ethyl, $R^1$=pentyl and $R^2$–$R^5$ simultaneously=ethyl, propyl or butyl, $R^1$=1-tert-butyl-1,1'-dimethylpropyl and $R^2$–$R^5$ simultaneously=ethyl and $R^1$=dodecyl and $R^2$–$R^5$ simultaneously=butyl.

The radical of the formula II is understood as meaning radicals such as, for example, cyclopropyl, cyclobutyl, cyclopentyl, cyclohexyl, cycloheptyl, cyclooctyl, cyclononyl or cyclodecyl, which can optionally be substituted by one or more alkyl radicals having 1 to 6 carbon atoms.

Het is understood as meaning monocyclic 5- to 6-membered or bicyclic 8- to 10-membered saturated, unsaturated or partially unsaturated heterocyclic radicals having 1 to 3 identical or different heteroatoms selected from the group consisting of nitrogen, oxygen and sulphur. Het preferably contains 1 or 2 nitrogen atoms.

Monocyclic heterocyclic radicals are e.g. pyrrole, pyrroline, pyrrolidine, pyridine, tetrahydropyridine, piperidine, pyrazole, imidazole, pyrazoline, imidazoline, pyrazolidine, imidazolidine, pyridazine, pyrimidine, pyrazine, piperazine, oxazole, oxazoline, oxazolidine, isoxazole, isoxazoline, isoxazolidine, morpholine, thiazole, isothiazol, thiazoline, isothiazoline, thiazine, furan, tetrahydrofuran, thiophene, thiolane, dioxane, pyran, thiopyran, 1,3-dioxolene, 1,2-oxa-thiolane, 1,2,3-triazole, 1,2,4-triazole, 1,2,4-thiadiazole, 1,3,4-thiadiazole, 1,3,5-, 1,2,4- and 1,2,3-triazine. Preferred radicals are: pyrrole, pyrroline, pyrrolidine, pyridine, tetrahydropyridine, piperidine, pyrazole, imidazole, pyrazoline, imidazoline, pyrazolidine, imidazolidine, pyridazine, pyrimidine, pyrazine, piperazine, morpholine and 1,3,5-triazine.

Bicyclic heterocyclic radicals are e.g. benzothiophene, benzofuran, indole, isoindole, indolizine, indazole, benzimidazole, quinoline, isoquinoline, phthalazine, quinoxaline, quinazoline, cinnoline, chroman, 4H-chromene, coumarone, thionaphthene, pyrrolo[1,5-a]pyrimidine, imidazo[2,1-b]oxazole, purine and pteridine.

Alkyl can be straight-chain or branched. The same applies to radicals derived therefrom such as e.g. alkanoyl.

If not stated otherwise, halogen is chlorine, bromine, iodine or fluorine, preferably fluorine, chlorine or bromine.

Preferred compounds of the formula I are those where $R^1$ is $(C_1-C_{10})$-alkyl, $(C_1-C_8)$-alkanoyl, $(C_6-C_{10})$-aryl or Het having 1 or 2 nitrogen atoms, each of which can be substituted one to six times by halogen, —OH, —NH$_2$, —NH—CO—R$^7$, —O—CO—R$^7$ and —N—(R$^8$)$_2$, where R$^7$ is $(C_1-C_6)$-alkyl and R$^8$ independently of one another, is hydrogen or $(C_1-C_4)$-alkyl, or the radical of the formula II

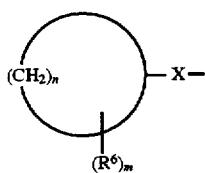

in which
n is an integer from 3 to 10,
m is 1,
$R^6$ is $(C_1-C_6)$-alkyl which is optionally substituted one to six times by halogen or —NH—CO—$R^7$ where $R^7=(C_1-C_6)$-alkyl and
X is absent or $(C_1-C_{10})$-alkyl, and
$R^2$ and $R^3$, $R^4$ and $R^5$ are hydrogen, lithium, sodium or $(C_1-C_5)$-alkyl,
compounds of the formula I being excluded where
$R^1$=methyl and $R^2-R^5$ simultaneously=methyl, ethyl, propyl, isopropyl, butyl or isobutyl or $R^2$ and $R^3$=ethyl or isopropyl and $R^4$ and $R^5$=methyl,
$R^1$=ethyl and $R^2-R^5$ simultaneously=ethyl, propyl, isopropyl, butyl or isobutyl or $R^2$ and $R^3$=ethyl and $R^4$ and $R^5$=methyl,
$R^1$=isopropyl and $R^2$ and $R^3$=isopropyl and $R^4$ and $R^5$=methyl,
$R^1$=butyl and $R^2-R^5$ simultaneously=ethyl, isopropyl or butyl,
$R^1$=isobutyl and $R^2-R^5$ simultaneously=ethyl,
$R^1$=pentyl and $R^2-R^5$ simultaneously=ethyl, propyl or butyl and
$R^1$=1-tert-butyl-1,1'-dimethylpropyl and $R^2-R^5$ simultaneously=ethyl.

Particularly preferred compounds of the formula I are those where
n is an integer 7, 8, 9 or 10,
m is 1,
$R^1$ is $(C_1-C_5)$-alkyl, phenyl, naphthyl or a radical from the group consisting of piperidinyl, pyrolidinyl, piperazinyl, pyridinyl, morpholinyl, imidazole and pyrazole,
$R^2$, $R^3$, $R^4$ and $R^5$ simultaneously are hydrogen, sodium or lithium.

Particularly preferred compounds are those from the following group:
tetraethyl N-cycloheptylimidobisphosphate,
tetraethyl N-[2-(N',N'-diisopropylamino) ethyl] imidobisphosphate,
tetraethyl N-[2-(N'-morpholino)ethyl]imidobisphosphate,
tetraethyl N-[2-(2-pyridyl) ethyl]imidobisphosphate,
tetraethyl N-[3-(N'-morpholino)propyl]imidobisphosphate,
tetraethyl N-cyclohexylimidobisphate,
tetraethyl N-[1-(cyclohexyl) ethyl]imidobisphosphate,
tetraethyl N-heptylimidobisphosphate,
tetraethyl N-benzylimidobisphosphate,
N-benzylimidobisphosphoric acid,
N-[2-(N',N'-diisopropylamino)ethyl]imidobisphosphoric acid,
N-[2-(N'-morpholino)ethyl]imidobisphosphoric acid,
N-[2-(2-pyridyl)ethyl]imidobisphosphoric acid,
N-[3-(N'-morpholino)propylimidobisphosphoric acid,
tetralithium N-cycloheptylimidobisphosphate,
tetralithium N-cyclohexylimidobisphosphate,
tetralithium N-[1-(cyclohexyl) ethyl]imidobisphosphate,
tetralithium N-heptylimidobisphosphate,
tetralithium N-benzylimidobisphosphate,
tetralithium N-[2-(N,N'-diisopropylamino) ethyl] imidobisphosphate,
tetralithium N-[2-(N,N'-dibutylamino)ethyl] imidobisphosphate.

Suitable physiologically tolerable salts of the compounds of the formula I are, for example, alkali metal, alkaline earth metal or ammonium salts, and those of physiologically tolerable, organic ammonium or triethylamine bases.

The invention further relates to a process for the preparation of compounds of the formula I

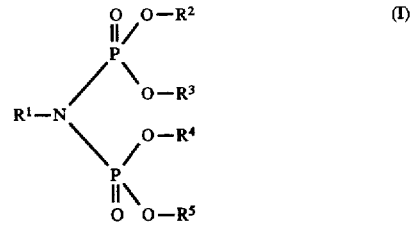

and their physiologically tolerable salts, where
$R^1$ is $(C_1-C_{10})$-alkyl, $(C_1-C_8)$-alkanoyl, $(C_6-C_{10})$-aryl or Het, each of which can be substituted one to six times by halogen, —OH, —$NH_2$, —NH—CO—$R^7$, —O—CO—$R^7$ and —N—$(R^8)_2$, where $R^7$ is $(C_1-C_6)$-alkyl and $R^8$, independently of one another, is hydrogen or $(C_1-C_4)$-alkyl, or
the radical of the formula II

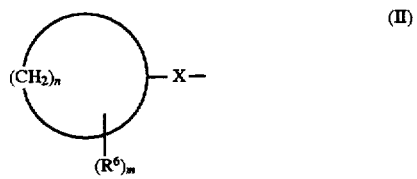

in which
n is an integer from 3 to 10,
m is zero to 3,
$R^6$, independently of one another, is $(C_1-C_6)$-alkyl, which is optionally substituted one to six times by halogen or —NH—CO—$R^7$ where $R^7=(C_1-C_6)$-alkyl and
X is absent or is $(C_1-C_{10})$-alkyl, and
$R^2$, $R^3$, $R^4$ or $R^5$, independently of one another, are hydrogen, $(C_1-C_5)$-alkyl, lithium, sodium, potassium or Si(R) , where R=$(C_1-C_5)$-alkyl, which comprises
a) reacting alkyl imidobisphosphites of the formula III, accessible according to the process described by L. K. Nikonorova et al., J. Gen. Chem. USSR 46, 1976, 1012–1014

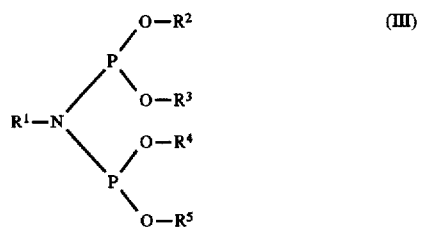

in which
$R^1$ has the abovementioned meaning and
$R^2$, $R^3$, $R^4$ and $R^5$ are $(C_1-C_5)$-alkyl, with an oxygen-transferring agent to give the compound of the formula I, b) optionally reacting the compounds thus obtained in an inert solvent with the aid of an alkylhalosilane to give a tetratrimethylsilyl imidobisphosphate, and c) then optionally hydrolyzing or converting into the corresponding salts with the aid of a basic salt.

In reaction step a), a procedure is best used in which the compound of the formula III is reacted in equimolar amounts or with an up to 70% excess of hydrogen peroxide (35%) in alcohols such as methanol, ethanol, n-propanol, i-propanol, n-butanol or i-butanol to give the corresponding N-substituted tetraalkyl imidobisphosphates of the formula I. The reaction temperatures here are between −50° C. and +70° C., in particular 30° C., and the reaction times are between 15 minutes and 4 hours, preferably between 1 and 3 hours. The crude products obtained can be purified either by distillation, crystallization or preparative column chromatography.

In reaction step b), a procedure is best used in which the compounds obtained according to reaction step a) are reacted with a four- to six-fold excess of an alkylsilane such as, for example, chloro-, bromo- or iodo-trimethylsilane. Solvents suitable for this purpose are toluene, o-, m- or p-xylene, chlorobenzene or acetonitrile; acetonitrile is preferred, it being possible to employ the solvents in dried form. The reaction temperatures here are between 0° C. and 70° C., preferably 20° C. to 30° C. The reaction times are between 1 hour and 24 hours, preferably between 4 hours and 18 hours. The respective solvent and the excess of silane are then removed in vacuo. The desired product of the formula I is obtained as a residue.

In reaction step c), a procedure is best used in which the compounds obtained according to reaction h) are dissolved in a solvent such as, for example, an alcohol, preferably methanol, ethanol, n-propanol, i-propanol, n-butanol or i-butanol, particularly preferably methanol, ethanol or i-propanol, and allowed to stand at a temperature of 10° C. to 30° C., preferably at 25° C., until the compound of the formula I crystallizes, or 4 mol equivalents to 100 mol equivalents, preferably 4 mol equivalents to 20 mol equivalents, of water are added to the solution at a temperature of 10° C. to 30° C., preferably at 25° C., and it is allowed to stand until the compound crystallizes. The compounds thus obtained are then suspended in an inert solvent such as, for example, n-hexane, n-heptane, methylcyclohexane, petroleum ether (40°–60° C.), preferably n-hexane or petroleum ether (40°–60° C.) and filtered or the compounds obtained according to reaction step b) are dissolved directly in a solvent such as, for example, n-hexane, n-heptane, methylcyclohexane or petroleum ether (40°–60° C.), preferably n-hexane or petroleum ether (40°–60° C.). 4 to 10 mol equivalents, preferably 4 mol equivalents, of an alkali metal alkoxide such as, for example, lithium methoxide, sodium methoxide, potassium methoxide, preferably lithium methoxide, sodium methoxide or potassium methoxide, particularly preferably lithium methoxide or sodium methoxide, dissolved in an alcohol such as, for example, methanol or ethanol, preferably methanol, are added to this solution. The reaction temperatures are between −10° C. and 40° C., preferably between −5° C. and 30° C. The reaction times are between 1 hour and 20 hours, preferably between 1 hour and 14 hours. The compounds of the formula I as a rule crystallize from the reaction solution in highly pure form.

The invention also relates to pharmaceuticals which contain at least one compound of the formula I and/or at least one of its physiologically tolerable salts, in addition to pharmaceutically suitable and physiologically tolerable auxiliaries and excipients, diluents and/or other active compounds.

The invention further relates to the use of the compounds of the formula I and their physiologically tolerable salts for the prophylaxis and treatment of osteoporosis and hypercalcemia, preferably osteoporosis.

The pharmaceuticals according to the invention can be administered intravenously, intramuscularly, intraperitoneally, subcutaneously, intraarticularly, periarticularly, rectally or orally.

The pharmaceuticals according to the invention for the treatment of degenerative joint disorders are prepared by bringing at least one compound of the formula I and/or one of its physiologically tolerable salts into a suitable administration form, if appropriate using further auxiliaries and/or excipients. The auxiliaries and excipients derive from the group consisting of excipients, preservatives and other customary auxiliaries.

For example, for oral administration forms auxiliaries such as starches, e.g. potato, corn or wheat starch, cellulose or its derivatives, in particular microcrystalline cellulose, silica, various sugars such as lactose, magnesium carbonate and/or calcium phosphates can be used. It is furthermore advantageous to add to the oral administration forms auxiliaries which improve the tolerability of the medicaments, such as e.g. mucigenous agents and resins. To improve tolerability, the medicaments can also be administered in the form of enteric-resistant capsules. Moreover, it may be advantageous to add to the administration form, or to a component of a combination preparation, a release-delaying agent, if appropriate in the form of permeable membranes, such as e.g. those based on cellulose or polystyrene resin, or ion exchangers.

The dose of the pharmaceuticals according to the invention to be administered is dependent on various factors such as administration form of the medicaments and condition, weight and severity of the disorder of the patient. A daily dose of about 5,000 mg of the pharmaceuticals according to the invention should only be exceeded, however, for a short time. A preferred dose is about 10 to 2,500 mg as a daily dose for a human of bodyweight about 70 kg. The administration of the daily dose of the pharmaceuticals according to the invention can be carried out in the form of a single administration or in several small doses. Administration in 3 to 8 doses per day is preferred.

The activity of the compounds of the formula I according to the invention is determined in vitro in the following experiment:

Hydroxyapatite adsorption test (Shinoda et al., Calcf. Tissue Int. 1983, Vol. 35, 87–99):

65 mg of hydroxyapatite were suspended in 200 ml of 0.01M barbital buffer (pH 7.0) which contains 0.115M KCl, and stirred at 37° C. for 24 hours. The substances to be tested (0.075 mol per mole of hydroxyapatite) were then added to the equilibrated suspension and it was stirred for a further 2 hours. The suspension was passed through a filter (0.45 μm pore size), and the hydroxyapatite was scraped from the filter and then suspended again in 75 ml of the same barbital buffer and stirred at 37° C. After 1 hour, the calcium concentration of the buffer was determined using an automatic calcium concentration analyzer (Hitachi model 7050). From this value, the ability to inhibit calcium release was calculated for the tested compounds. The determination was repeated 3× for each compound. The value for methanediphosphonic acid is given as a standard.

The results are compiled in Table 1.

TABLE 1

| Compound | Calcium concentration [mg/dl] |
|---|---|
| Control | 0.663 ± 0.008 |
| Methanediphosphonic acid | 0.537 ± 0.010* |
| Example 18 | 0.603 ± 0.006* |
| Example 20 | 0.607 ± 0.006* |
| Example 21 | 0.553 ± 0.010* |
| Example 22 | 0.513 ± 0.010* |

*significant difference 1%

All tested compounds significantly inhibited calcium release from hydroxyapatite.

EXAMPLES

1) Tetraethyl N-cycloheptylimidobisphosphate
  a) Tetraethyl N-cycloheptylimidobisphosphite 8.0 g (71 mmol) of cycloheptylamine and 14.8 g (142 mmol) of triethylamine are initially introduced into 80 ml of dichloromethane at 0° C. 22.0 g (142 mmol) of diethyl monochlorophosphite, dissolved in 20 ml of dichloromethane, are added dropwise to this at 0° C. After addition is complete, the reaction solution is allowed to come to room temperature and is stirred overnight. The salt formed is then filtered off. 16.5 g (85% of theory) of triethylamine hydrochloride are isolated in this process. In order to isolate further hydrochloride, the solution is cooled at −30° C. for 4 hours. Freshly precipitated hydrochloride is filtered off with suction through Perlite and the solution is concentrated (12 mbar). In this manner, 20.7 g of tetraethyl N-cycloheptylimidobisphosphite ($^{31}$P-NMR (CDCl$_3$): δ=146.7 ppm) are obtained as a crude product. This crude product is directly reacted further as described under b).

b) Tetraethyl N-cycloheptylimidobisphosphate 20.7 g (58 mmol) of crude product from a) are dissolved in 150 ml of methanol and added dropwise to a solution of 22 g (about 50% excess) of 35% strength hydrogen peroxide solution in 100 ml of methanol such that the reaction temperature does not exceed 30°. After the dropwise addition is complete, the mixture is stirred for 1 hour and 200 ml of methanol are removed in vacuo (12 mbar, not to dryness). The residue is taken up in 200 ml of dichloromethane and extracted 3 times with 80 ml of water each time. The dichloromethane phase is dried over sodium sulfate and evaporated (12 mbar). 18 g of crude product are obtained as an oil. The crude product is purified by distillation.

C$_{15}$H$_{33}$NO$_6$P$_2$ (385.4), yield: 10.0 g (44.1%), b.p. 137°–139° C./0.06 mbar; MS: (FAB) 386 (70) M$^+$, 290 (30) [M-cycloheptyl]$^+$; EA: calc. C=46.8, H=8.6, N=3.6, found C=46.9, H=8.4, N=3.7%. $^1$H-NMR (CDCl$_3$): δ=1.35 (t, $^3$J$_{HH}$=7.0 Hz, 12 H), 1.40–1.50 (m, 2H), 1.50–1.60 (m, 4H), 1.67–1.79 (m, 2H), 1.84–1.96 (m, 2H), 2.20–2.35 (m, 2H), 3.58 (m, 1H), 4.13 (m, 8H) ppm; $^{13}$C-NMR (CDCl$_3$): δ=16.0 (CH$_3$ (OEt)), 25.5 (CH$_2$), 26.9 (CH$_2$), 34.8 (CH$_2$), 61.9 (CH), 62.8 (CH$_2$ (OEt)) ppm; $^{31}$P-NMR (CDCl$_3$): δ=3.55 ppm.

The following compounds of examples 2–10 were prepared in an analogous manner. In the case of compounds which it was not possible to purify by distillation, purification was carried out by preparative column chromatography.

2) Tetraethyl N-butylimidobisphosphate

C$_{12}$H$_{29}$NO$_6$P$_2$ (345.3), yield: 15.5 g (84.7%), b.p. 120°–123° C./0.1 mbar; MS: (FAB) 345 (70) M$^+$; EA: calc. C=41.7, H=8.4, N=4.1, found C=41.7, H=8.4, N=4.8; $^1$H-NMR (CDCl$_3$): δ=0.93 (t, $^3$H$_{HH}$=7.3 Hz, 3H), 1.30 (m, 2H), 1.35 (t, $^3$J$_{HH}$=7.0 Hz, 12H), 1.69 (m, 2H), 3.31 (m, 2H), 4.15 (m, 8H) ppm; $^{13}$C-NMR (CDCl$_3$): δ=13.60 (CH$_3$), 15.96 (CH$_3$ (OEt)), 19.81 (CH$_2$), 32.95 (CH$_2$), 47.57 (CH$_2$), 63.08 (CH$_2$ (OEt)) ppm; $^{31}$P-NMR (CDCl$_3$): δ=3.98 ppm.

3) Tetraethyl N-[2-(N',N'-diisopropylamino) ethyl] imidobisphosphate

The crude product was purified on an acetone/silica gel column.

C$_{16}$H$_{38}$N$_2$O$_6$P$_2$ (416.5), yield: 14.9 g (71.2%), MS: (FAB) 416 (60) M$^+$; $^1$H-NMR (CDCl$_3$): δ=1.03 (d, $^3$J$_{HH}$=6.4 Hz, 12H), 1.36 (t, $^3$J$_{HH}$=7.0 Hz, 12H), 2.67 (m, 2H), 2.98 (m, $^3$J$_{HH}$=6.4 Hz, 2H), 3.24 (m, 2H), 4.15 (m, 8H) ppm; $^{13}$C-NMR (CDCl$_3$): δ=16.00 (CH$_3$ (OEt)), 20.66 (CH$_3$), 45.69 (CH$_2$), 48.64 (CH$_2$), 49.62 (CH), 63.14 (CH$_2$ (OEt)) ppm; $^{31}$P-NMR (CDCl$_3$): δ=4.33 ppm.

4) Tetraethyl N-[2-(N'-morpholino) ethyl] imidobisphosphate

The crude product was purified on an ethyl acetate/ethanol=1:1 silica gel column.

C$_{14}$H$_{32}$N$_2$O$_7$P$_2$ (402.4), yield: 11.3 g (40.1%); MS (FAB): 402 (70) M$^+$; $^1$H-NMR (CDCl$_3$): δ=1.36 (t, $^3$J$_{HH}$=7.0 Hz 12H), 2.52 (m, 4H), 2.63 (m, 2H), 3.48 (m, 2H), 3.68 (m, 4H), 4.16 (m, 8H) ppm; $^{31}$P-NMR (CDCl$_3$): δ=4.54 ppm.

5) Tetraethyl N-[2-(2-pyridyl) ethyl]imidobisphosphate

The crude product was purified on an ethyl acetate/ethanol=1:1 silica gel column.

C$_{15}$H$_{28}$N$_2$O$_6$P$_2$ (394.4), yield: 14.7 g (53.3%); $^1$H-NMR (CDCl$_3$): δ=1.37 (t, $^3$J$_{HH}$=7.0 Hz, 12H), 3.22 (m, 2H), 3.73 (m, 2H), 4.18 (m, 8H), 7.12 (m, 1H), 7.23 (m, 1H), 7.59 (m, 1H), 8.52 (m, 1H) ppm; $^{31}$P-NMR (CDCl$_3$): δ=4.24 ppm.

6) Tetraethyl N-[3-(N'-morpholino)propyl] imidobisphosphate

The crude product was purified on an ethyl acetate/ethanol=1:1 silica gel column.

C$_{15}$H$_{34}$N$_2$O$_7$P$_2$ (416.4), yield: 14.9 g (54.5%); $^1$H-NMR (CDCl$_3$): δ=1.35 (t, $^3$J$_{HH}$=7.0 Hz, 12H), 1.91 (m, 2H), 2.35 (t, 2H), 2.43 (m, 4H), 3.39 (m, 2H), 3.70 (m, 4H), 4.14 (m, 8H) ppm; $^{31}$P-NMR (CDCl$_3$): δ=4.46 ppm.

7) Tetraethyl N-cyclohexylimidobisphosphate

C$_{14}$H$_{31}$NO$_6$P$_2$ (371.4), yield: 18 g (69.4%), b.p. 136° C./0.1 mbar; $^1$H-NMR (CDCl$_3$): δ=1.20 (m, 4H), 1.34 (t, $^3$J$_{HH}$=7.0 Hz, 12H), 1.80 (m, 4H), 2.16 (m, 2H), 3.50 (m, $^3$J$_{HH}$=19.1 Hz, 1H), 4.13 (m, 8H) ppm; $^{31}$P-NMR (CDCl$_3$): δ=4.08 ppm.

8) Tetraethyl N-[1-(cyclohexyl)ethyl]imidobisphosphate

C$_{16}$H$_{35}$NO$_6$P$_2$ (399.3), b.p. 142° C./0.1 mbar, yield: 19.7 g (69.8%); $^1$H-NMR (CDCl$_3$): δ=1.19 (m, 4H), 1.34 (t, $^3$J$_{HH}$=7.0 Hz, 12H), 1.42 (d, 3H), 1.69 (m, 4H), 2.06 (m, 2H), 3.51 (m, 1H), 4.05 (m, 1H), 4.13 (m, 8H) ppm; $^{31}$P-NMR (CDCl$_3$): δ=4.75 ppm.

9) Tetraethyl N-heptylimidobisphosphate

C$_{15}$H$_{35}$NO$_6$P$_2$ (387.4), yield: 29 g (56%), b.p.: 147°–150° C./0.15 mbar; $^1$H-NMR (CDCl$_3$): δ=0.88 (t, 3H), 1.28 (m, 8H), 1.35 (t, $^3$J$_{HH}$=7.0 Hz, 12H), 1.69 (m, 2H), 3.30 (m, 2H), 4.15 (m, 8H) ppm; $^{31}$P-NMR (CDCl$_3$): δ=4.24 ppm.

10) Tetraethyl N-benzylimidobisphosphate

During working up, the low-boiling components were removed at 130° C./10$^{-3}$ mbar and tetraethyl N-benzylimidobisphosphate was thus obtained in pure form.

C$_{15}$H$_{27}$NO$_6$P$_2$ (379.3), yield: 17.1 g (86.3%); $^1$H-NMR (CDCl$_3$): δ=1.21 (t, $^3$J$_{HH}$=7.0 Hz, 12H), 4.08 (m, 8H), 4.56 (t, $^3$J$_{PH}$=12.5 Hz, 2H), 7.29 (m, 3H), 7.53 (m, 2H) ppm; $^{31}$P-NMR (CDCl$_3$): δ=3.98 ppm.

11) N-[2-(N',N'-Diisopropylamino)ethyl] imidobisphosphoric acid
  a) Tetratrimethylsilyl N-[2-(N',N'-diisopropylamimo) ethyl]imidobisphosphate 2.2 g (5.3 mmol) of tetraethyl N-[2-(N',N'-diisopropylamino)ethyl]imidobisphosphate are dissolved in 30 ml of anhydrous acetonitrile. 4.9 g=4.2 ml (31.8 mmol) of bromotrimethylsilane are added to this solution in the course of 1 hour at 25° C. The reaction is then stirred at this temperature for 18 hours. At the end of the reaction, the solvent and excess bromotrimethylsilane are stripped off at 0.06 mbar/40° C. The residue is waxy.

b) N-[2-(N',N'-Diisopropylamino)ethyl] imidobisphosphoric acid 1.5 g (0.76 mmol) of the silyl ester from a) are dissolved in 30 ml of i-propanol. 2.1 ml (120 mmol) of water are added dropwise to this solution and it is stirred for 4 hours at 25° C. 20 ml of ethyl acetate are then added and the mixture is allowed to stand for about 1 week to crystallize. The crystals which are deposited are filtered off with suction under protective gas and dried at 0.06 mbar/25° C.

$C_8H_{22}N_2O_{16}P_2$ (304.1), yield: 420 mg (26.3%), m.p.: 143° C.; MS (FAB): 304 (90) M$^+$; EA (3H$_2$O): calc. C=26.8, H=7.8, N=7.8, found C=27.1, H=6.8, N=7.7; $^1$H-NMR (D$_2$O): δ=1.36 (dd, $^3J_{HH}$=6.6 Hz, 12H), 3.29 (t, 2H), 3.62 (tt, $^3J_{HH}$=13.5 Hz, 2H), 3.73 (m, 2H) ppm; $^{31}$P-NMR (D$_2$O): δ=3.88 ppm.

12) N-[2-(N'-Morpholino)ethyl]imidobisphosphoric acid a) Tetratrimethylsilyl N-[2-(N'-morpholino)ethyl] imidobisphosphate 2.12 g (5.26 mmol) of tetraethyl N-[2-(N'-morpholino)ethyl]imidobisphosphate are reacted as described under 11a).

b) N-[2-(N'-Morpholino)ethyl]imidobisphosphoric acid 30 ml of methanol are added to the residue obtained under a) and the mixture is stirred for 2 hours at 25° C. During this process the product crystallizes as a colorless powder. The substance is filtered off in air, washed with petroleum ether (40°–60° C.) and dried in air.

$C_6H_{16}N_2O_7P_2$ (290.2), yield: 990 mg (64.7%), m.p.: 203° C.; MS (FAB): 290 (95) M$^+$; EA: calc. C=24.8, H=5.5, N=9.4, found C=24.9, H=5.3, N=9.4; $^1$H-NMR (D20): δ=3.20 (m, 2H), 3.36 (t, 2H), 3.60 (m, 2H), 3.62 (tt, $^3J_{HH}$=13.5 Hz, 2H), 3.81 (m, 2H), 4.12 (m, 2H) ppm; $^{31}$P-NMR. δ=3.32 ppm.

13) N-[2-(2-Pyridyl) ethyl]imidobisphosphoric acid a) Tetratrimethylsilyl N-[2-(2-pyridyl) ethyl] imidobisphosphate 1.61 g (5.26 mmol) of tetraethyl N-[2-(2-pyridyl)ethyl] imidobisphosphate are reacted as described under 11a).

b) N-[2-(2-Pyridyl) ethyl]imidobisphosphoric acid 30 ml of methanol are added to the residue obtained under a) and the mixture is stirred for 2 hours at 25° C.; during the course of this the product crystallizes as a colorless powder. The substance is filtered off in air, washed with petroleum ether (40°–60° C.) and dried in air. $C_7H_{12}N_2O_6P_2$ (282.1), yield: 650 mg (46.6%), m.p.: 186° C.; MS (FAB): 282 (90) M$^+$; EA (½ H$_2$O) calc. C =28.8, H=4.5, N=9.6, found C=28.8, H=4.3, N=9.4; $^1$H-NMR (D$_2$O): δ=3.39 (t, 2H) 3.65 (tt $^3J_{PH}$=13.5 Hz 2H) 7.88 (m, 1H), 7.96 (m, 1H), 8.47 (m, 1H), 8.63 (m, 1H) ppm; $^{31}$P-NMR (D$_2$O): δ=3.26 ppm.

14) N-[3-(N'-Morpholino)propyl]imidobisphosphoric acid a) Tetratrimethylsilyl N-[3 -(N'-morpholino) propyl] imidobisphosphate 2.19 g (5.3 mmol) of tetraethyl N-[3-(N'-morpholino) propyl]imidobisphosphate are reacted as described under 11a).

b) N-[3-(N'-Morpholino)propyl]imidobisphosphoric acid 20 ml of methanol are added to the residue obtained under a), and the mixture is stirred for 2 hours at 25° C.; during the course of this the product crystallizes as a colorless powder. The substance is filtered off, washed with 10 ml of methanol and then 10 ml of petroleum ether (40°–60° C.) and dried in air.

$C_7H_{18}N_2O_7P_2$ (304.2), yield: 450 mg (31.3%), m.p.: 75° C.; MS (FAB) 304 (60) M$^+$; $^1$H-NMR (D$_2$O): δ=2.09 (m, 2H), 3.14 (m, 2H) 3.26 (m, 2H), 3.39 (tt, $^3J_{PH}$=13.5 Hz, 2H), 3.53 (m, 2H), 3.81 (m, 2H), 4.12 (m, 2H) ppm; $^{31}$P-NMR (D$_2$O): δ=3.72 ppm.

15) Tetralithium N-cycloheptylimidobisphosphate a) Tetratrimethylsilyl N-cycloheptylimidobisphosphate 2.03 g (5.26 mmol) of tetraethyl N-cycloheptylimidobisphosphate are reacted as described under 11a).

b) Tetralithium N-cycloheptylimidobisphosphate

The reaction is carried out as described under 17b). $C_7H_{13}NO_6P_2Li_4$ (296.9), yield: 1.7 g (77%), m.p.: >230° C.; EA (4 CH$_3$OH): calc.c=31.0, H=6.8, N=3.3, found C=31.8, H=6.2, N=3.8; $^1$H-NMR: δ=1.34–1.68 (m, 8H), 1.82–2.12 (m,4H), 3.41 (m, $^3J_{PH}$=20.8 Hz, IH) ppm; $^{31}$P=NMR (D$_2$O): δ=8.01 ppm.

16) Tetralithium N-cyclohexylimidobisphosphate a) Tetratrimethylsilyl N-cyclohexylimidobisphosphate 1.95 g (5.26 mmol) of tetraethyl N-cyclohexylimidobisphosphate are reacted as described under 11a).

b) Tetralithium N-cyclohexylimidobisphosphate

The reaction is carried out as described under 17b). $C_6H_{11}NO_6P_2Li_4$ (282.8), yield: 1.8 g (90%), m.p.: >230° C.; EA (3 CH$_3$OH): calc. C=28.5, H=6.1, N=3.7, found C=28.8, H=5.7, N=3.8; $^1$H-NMR (D$_2$O): δ=1.00–1.33 (m, 3H), 1.53 (m, 1H), 1.74 (m, 4H), 1.94 (m, 2H), 3.27 (m, $^3J_{PH}$=21.0 Hz, 1H) ppm; $^{31}$P-NMR (D$_2$O): δ=7.96 ppm.

17) Tetralithium N-[1-(cyclohexyl)ethyl]imidobisphosphate a) Tetratrimethylsilyl N-[1-(cyclohexyl)ethyl] imidobisphosphate 1.05 g (2.63 mmol) of tetraethyl N-[1-(cyclohexyl) imidobisphosphate are reacted as described under 11a).

b) Tetralithium N-[1-(cyclohexyl)ethyl] imidobisphosphate

The residue from a) is taken up in 15 ml of petroleum ether (40°–60° C.) and cooled to 0° C. 0.4 g of lithium methoxide dissolved in 3 ml of methanol is added to this solution, and the mixture is stirred for a further hour at 0° C. and then for 12 hours at 25° C. A gelatinous precipitate is formed. The petroleum ether is distilled off at 0.06 mbar/25° C., the residue is taken up in 15 ml of methanol and the solution is stirred for a further hour at 25° C. After filtration of the precipitate, a further 15 ml of petroleum ether (40°–60° C.) are added and the solid is precipitated by stirring and filtered again. A colorless powder is obtained in this process, which is dried at 0.06 mbar/25° C.

$C_8H_{15}NO_6P_2Li_4$ (310.8), yield: 890 mg (90%), m.p.: >230° C.; EA (2 CH$_3$OH): calc. C=32.0, H=6.2, H=3.7, found C=32.6, H=6.0, N=3.8; $^1$H-NMR (D$_2$O): δ=0.8 (m, 2H), 1.17 (m, 2H), 1.28 (d, 3H), 1.55–1.95 (m, 6H), 2.21 (m, 1H), 3.13 (m, $^3J_{PH}$=20.2 Hz, 1H) ppm; $^{31}$P-NMR (D$_2$O): δ=8.04 ppm.

18) Tetralithium N-heptylimidobisphosphate a) Tetratrimethylsilyl N-heptylimidobisphosphate 1.02 g (2.63 mmol) of tetraethyl N-heptylimidobisphosphate are reacted as described under 11a).

b) Tetralithium N-heptylimidobisphosphate

The reaction is carried out as described under 17b). For crystallization, the product is taken up in 15 ml of methanol, filtered and dried at 0.06 mbar/25° C. $C_7H_{15}NO_6P_2Li_4$ (298.9), yield: 450 mg (52%), m.p.: >230° C.; EA (CH$_3$OH): calc. C=29.0, H=5.8, N=4.2, found C=29.2, H=5.9, N=3.8; $^1$H-NMR (D$_2$O): δ=0.87 (t, 3H), 1.12–1.39 (m, 8H), 1.62 (m, 2H), 3.00 (m, $^3J_{PH}$=13.9 Hz, 2H) ppm; $^{31}$P-NMR (D$_2$O): δ=8.01 ppm.

19) Tetrasodium N-benzylimidobisphosphate a) Tetratrimethylsilyl N-benzylimidobisphosphate 1.05 g (2.63 mmol) of tetraethyl N-benzylimidobisphosphate are reacted as described under 11a).

b) Tetrasodium N-benzylimidobisphosphate

The residue is taken up in 10 ml of petroleum ether (40°–60° C.) and the solution is cooled to 0° C. 0.25 g of sodium methoxide dissolved in 3 ml of methanol is added to this solution in the course of 10 minutes. Directly after the addition, a two-phase system is formed, which homogenizes within 30 minutes. A waxy product is formed in the course of 2–3 hours, which becomes crystalline after 2 days. This product is filtered off with suction with the aid of a Schlenk frit and washed twice with 20 ml of acetone each time. A colorless crystalline product is obtained in this process, which is dried at 0.06 mbar/25° C.

$C_7H_7NO_6P_2Na_4$ (354.7), yield: 770 mg (78.5%), m.p.: <230° C.; $^1$H-NMR ($D_2O$): δ=4.40 (t, $^3J_{PH}$=12.5 HZ, 2H), 7.20–7.65 (m, 5H) ppm; $^{31}$P-NMR ($D_2O$): δ=7.60 ppm.

20) N-Benzylimidobisphosphoric acid

Preparation is carried out analogously to the process described under 1) and 11).

$C_7H_{11}NO_6P_2$ (267.1), yield: 526 mg (75%); $^{31}$P-NMR ($D_2O$): 3.86 ppm.

Tetralithium N-[2-(N',N'-diisopropylamino)ethyl] imidobisphosphate

Preparation is carried out analogously to the process described under 1) and 17).

$C_8H_{18}N_2O_6P_2Li_4$ (327.2), yield: 631 mg (80%); $^{31}$P-NMR ($D_2O$): 7.13 ppm.

22) Tetralithium N-[2-(N',N'-dibutylamino)ethyl] imidobisphosphate

Preparation is carried out analogously to the process described under 1) and 17).

$C_{10}H_{22}N_2O_6P_2Li_4$ (355.9), yield: 673 mg (72%); $^{31}$P-NMR ($D_2O$): δ=6.95 ppm.

We claim:

1. A compound of the formula I

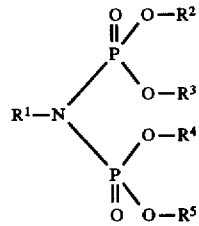

(I)

or its physiologically tolerable salts, where $R^1$ is ($C_1$–$C_{10}$)-alkyl, ($C_1$–$C_8$)-alkanoyl, each of which can be substituted one to six times by —$NH_2$, —NH—CO—$R^7$, and —N—($R^8$)$_2$, where $R^7$ is ($C_1$–$C_6$)-alkyl and $R^8$, independently of one another, is hydrogen or ($C_1$–$C_4$)-alkyl, and $R^2$, $R^3$, $R^4$ and $R^5$, independently of one another, are hydrogen, lithium, sodium, or potassium.

2. A compound of the formula I as claimed in claim 1, wherein $R^1$ is ($C_1$–$C_{10}$)-alkyl, ($C_1$–$C_8$)-alkanoyl, each of which can be substituted one to six times by —$NH_2$, —NH—CO—$R^7$, and —N—($R_8$)$_2$, where $R^7$ is ($C_1$–$C_6$)-alkyl and $R^8$ independently of one another, is hydrogen or ($C_1$–$C_4$)-alkyl, and $R^2$, $R^3$, $R^4$ and $R^5$, independently of one another, are hydrogen, lithium, or sodium.

3. A compound of the formula I as claimed in claims 1 or 2, from the group

N-[2-(N',N'-diisopropylamino)ethyl]imidobisphosphoric acid, tetralithium N-heptylimidobisphosphate, tetralithium N-[2-(N,N'-diisopropylamino)ethyl]-imidobisphosphate, tetralithium N-[2-(N,N'-dibutylamino)ethyl] imidobisphosphate.

4. A method of treating or prophylactic treatment of degenerative joint disorders by administration of a compound of claim 1.

5. The method according to claim 4, wherein the treatment is prophylactic.

6. A method of treating or prophylactic treatment of osteoporosis or hypercalcemia by administration of a compound of claim 1.

7. The method according to claim 6, wherein the treatment is prophylactic.

8. A method of inhibiting calcium release from hydroxyapatite by administration of a compound according to claim 1.

9. A pharmaceutical, containing an effective amount of at least one compound of the formula I as claimed in claim 1, or at least one physiologically tolerable salt of such a compound, in addition to pharmaceutically suitable and physiologically tolerable auxiliaries and excipients, diluents and/or other active compounds.

* * * * *

UNITED STATES PATENT AND TRADEMARK OFFICE
CERTIFICATE OF CORRECTION

PATENT NO. : 5,733,897
DATED : March 31, 1998
INVENTOR(S) : Christoph NAUMANN et al.

It is certified that error appears in the above-identified patent and that said Letters Patent is hereby corrected as shown below:

Claim 2, column 12, line 15, "$(R_8)_2$" should read --$(R^8)_2$--.

Signed and Sealed this

Eighth Day of June, 1999

Q. TODD DICKINSON

Attest:

Attesting Officer

Acting Commissioner of Patents and Trademarks